US00PP13023P2

(12) United States Plant Patent
Nuccio

(10) Patent No.: US PP13,023 P2
(45) **Date of Patent: *Oct. 1, 2002**

(54) CAMELLIA PLANT NAMED 'NUCCIO'S BELLA ROSSA'

(75) Inventor: Julius Nuccio, Sunset Beach, CA (US)

(73) Assignee: Nuccio's Nurseries, Inc., Sunset Beach, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/564,250

(22) Filed: May 4, 2000

(51) Int. Cl.[7] ..... A01H 5/00
(52) U.S. Cl. ..... Plt./245
(58) Field of Search ..... Plt./245

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new plant variety of Camellia with attractive red flowers.

1 Drawing Sheet

BACKGROUND OF THE INVENTION

The present invention relates to a new and distinct variety of Camellia and was discovered as a seedling in a controlled planting of *Camellia japonica* in Altadena, Calif. The parent cultivars are unknown *Camellia japonica*. The varietal denomination of the new variety is 'NUCCIO'S BELLA ROSSA'.

The genus Camellia is included in the family Theaceae which comprises about 25 genera of shrubs and trees, mostly tropical and subtropical, growing in the northern and southern hemispheres. Camellia comprises over 80 species of evergreen shrubs or trees, many of which possess desirable ornamental characteristics.

SUMMARY OF THE INVENTION

The new variety produces attractive red flowers. Asexual reproduction of the new variety by grafting and stem cuttings performed in Altadena, Calif. has confirmed that the distinctive characteristics of the new variety are stable and transmitted to succeeding generations.

BRIEF DESCRIPTION OF ILLUSTRATION

The accompanying illustration shows a flower of the new cultivar in a photo illustration as true to color as is reasonably possible to make in an illustration of this character.

DESCRIPTION OF THE NEW VARIETY

'NUCCIO'S BELLA ROSSA' has not been observed under all possible environmental, cultural, and light conditions. The following observations and descriptions are of a 14-year old plant grown in Altadena, Calif. In the description, color references are to *The Royal Horticultural Society Colour Chart* and terminology used in the color descriptions herein refers to plate numbers in this color chart. Phenotypic expression may vary with light intensity, cultural, and environmental conditions.

Plant

Form: Upright, fairly compact.
Growth: Medium growth rate: about 5 feet high by 3 feet wide at 10 years of age.
Diameter: About 3 feet.

Leaves:
- *Shape*.—Oval.
- *Size*.—Length — about 4 inches; width — about 3 inches.
- *Color*.—Upperside medium green near 147A to 147B; underside lighter near 147C.
- *Margin*.—Serrate.
- *Apex*.—Mucronate.
- *Base*.—Rounded.
- *Texture*.—Glabrous.
- *Vein color*.—Near Yellow-Green Group 149A.
- *Venation pattern*.—Midrib to margin.

Wood: New shoots are of amber color, near 23C to 23B.
Trunk:
- *Diameter*.—About 2½ inches.
- *Color*.—Brown, near Grey-Brown, Group 199B.
- *Texture*.—Generally smooth, with some roughness.
- *Branches*.—Size: About ½ inch in diameter. Crotch Angle: About 45° to about 60°. Texture: Generally smooth, with some roughness; somewhat rougher than trunk.
- *Roots*.—Roots develop in about 90 days.
- *Hardiness*.—Appears to be neither exceptionally more cold hardy or more cold sensitive, nor more heat tolerant or heat sensitive than most other *Camellia japonica* cultivars. However, 'NUCCIO'S BELLA ROSSA' has only been observed in Southern California (temperature range from about 25° F. to about 107° F.).

Flower

Bud:
- *Length*.—About 1 inch.
- *Width*.—About ½ inch.
- *Color*.—Same as the underside of the leaf, medium green near Yellow-Green Group 147C.

Sepals:
- *Number*.—5.
- *Length*.—About ¾ inch.
- *Width*.—About ⅝ inch.
- *Color*.—Near Green-Yellow Group 1D.

Size: About 4 inches to about 5½ inches.

Form: Formal Double. Petals are larger at base of flower, progressively smaller toward center, ending at center without stamens or pistil. About 55 to about 70 petals. Flowers are single.

Petal:

*Size*.—Ranges from about 1¼ inches by ½ inch to 2 inches by 2 inches.

*Texture*.—Glabrous.

*Shape*.—Notches at apex, tapering to a narrow, flat base.

*Color*.—Same for upper and lower surface, near Red Group 46B. Occasionally, lavender tones near margin of petals, near Purple-Violet Group 82C.

*Pedicel*.—None. 'NUCCIO'S BELLA ROSSA' is sessile.

Fragrance: None.

Lastingness of bloom: On plant — about 6 days; cut — about 4 days.

Reproductive organs: Plant is not fertile and has no stamen or stigma, produces no pollen and hips.

I claim:

1. A new plant of Camellia substantially as shown and described.

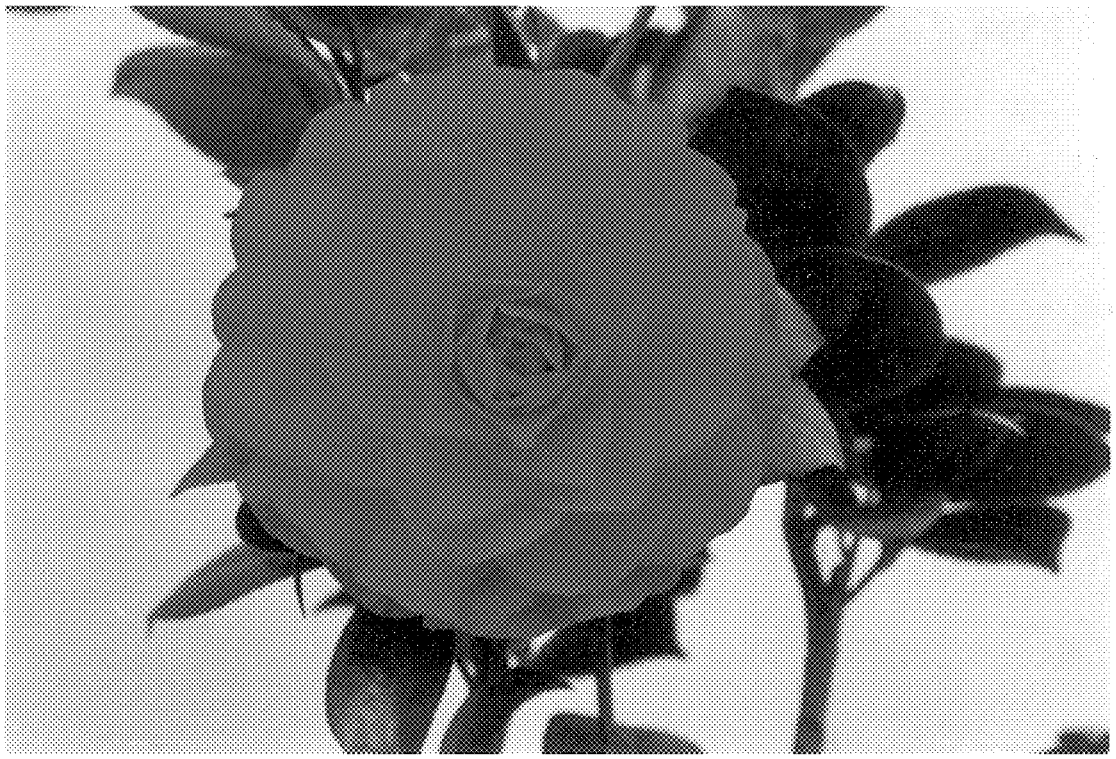

* * * * *